(12) United States Patent
Bennet et al.

(10) Patent No.: US 10,029,101 B2
(45) Date of Patent: Jul. 24, 2018

(54) SYSTEMS FOR THE DETECTION AND DELIVERY OF NEUROCHEMICAL AND ELECTRICAL SIGNALS FOR FUNCTIONAL RESTORATION

(71) Applicant: Mayo Foundation for Medical Education and Research, Rochester, MN (US)

(72) Inventors: Kevin E. Bennet, Rochester, MN (US); Kendall H. Lee, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 14/760,011

(22) PCT Filed: Jan. 9, 2014

(86) PCT No.: PCT/US2014/010882
§ 371 (c)(1),
(2) Date: Jul. 9, 2015

(87) PCT Pub. No.: WO2014/110263
PCT Pub. Date: Jul. 17, 2014

(65) Prior Publication Data
US 2015/0360032 A1 Dec. 17, 2015

Related U.S. Application Data (60) Provisional application No. 61/750,550, filed on Jan. 9, 2013.

(51) Int. Cl.
*A61N 1/36* (2006.01)
*A61N 1/05* (2006.01)

(52) U.S. Cl.
CPC ....... *A61N 1/36139* (2013.01); *A61N 1/0534* (2013.01); *A61N 1/0551* (2013.01)

(58) Field of Classification Search
CPC .... A61N 1/36; A61N 1/3605; A61N 1/36003; A61N 1/36139; A61N 1/0551; A61N 1/0534; A61B 5/145
(Continued)

(56) References Cited

U.S. PATENT DOCUMENTS 5,650,061 A 7/1997 Kuhr et al.
5,806,517 A 9/1998 Gerhardt et al.
(Continued)

FOREIGN PATENT DOCUMENTS

WO  WO 2010/083208  7/2010
WO  WO 2011/028608  3/2011
WO  WO 2015/021470  2/2015

OTHER PUBLICATIONS

International Preliminary Report on Patentability for PCT/US2014/010882, dated Jul. 23, 2015, 6 pages.
(Continued)

*Primary Examiner* — Mark W Bockelman
(74) *Attorney, Agent, or Firm* — Fish & Richardson P.C.

(57) ABSTRACT

This document provides methods and materials involved in detecting and delivering neurochemical signals, electrophysiological signals, ions, or combinations thereof within a mammal. For example, systems that can include one or more implantable devices containing probes configured to detect neurochemical signals (e.g., neurotransmitter concentrations), electrical signals, ions, or combinations thereof and one or more implantable devices containing electrodes and/or microfluidic delivery components configured to deliver neurochemical signals (e.g., neurotransmitters), electrical
(Continued)

signals, ions, or combinations thereof to one or more locations within a mammal are provided.

14 Claims, 6 Drawing Sheets

(58) Field of Classification Search
USPC .................................................. 607/48–49
See application file for complete search history.

(56) References Cited

U.S. PATENT DOCUMENTS

| | | | |
|---|---|---|---|
| 6,164,284 A * | 12/2000 | Schulman | A61B 5/0031 |
| | | | 128/899 |
| 7,209,788 B2 * | 4/2007 | Nicolelis | A61B 5/0478 |
| | | | 128/905 |
| 7,440,806 B1 | 10/2008 | Whitehurst et al. | |
| 7,747,318 B2 | 6/2010 | John et al. | |
| 7,899,545 B2 | 3/2011 | John | |
| 7,901,368 B2 | 3/2011 | Flaherty et al. | |
| 8,140,152 B2 | 3/2012 | John et al. | |
| 8,315,703 B2 | 11/2012 | Lozano | |
| 8,359,100 B2 | 1/2013 | Cameron et al. | |
| 8,433,415 B2 | 4/2013 | Leiter et al. | |
| 8,473,060 B2 | 6/2013 | Leiter et al. | |
| 2002/0013612 A1 | 1/2002 | Whitehurst | |
| 2004/0108223 A1 | 6/2004 | Jansson | |
| 2006/0009814 A1 | 1/2006 | Schulman | |
| 2006/0173509 A1 | 8/2006 | Lee et al. | |
| 2006/0195157 A1 | 8/2006 | Lee et al. | |
| 2006/0241717 A1 | 10/2006 | Whitehurst et al. | |
| 2007/0026440 A1 | 2/2007 | Broderick et al. | |
| 2008/0179197 A1 | 7/2008 | Wu | |
| 2008/0258116 A1 | 10/2008 | Viticoli et al. | |
| 2008/0288023 A1 | 11/2008 | John | |
| 2010/0032316 A1 | 2/2010 | Wu | |
| 2010/0312305 A1 | 12/2010 | Leiter et al. | |
| 2012/0088983 A1 | 4/2012 | Jung et al. | |
| 2012/0165634 A1 | 6/2012 | Lee et al. | |
| 2013/0023745 A1 | 1/2013 | Lee et al. | |
| 2016/0192872 A1 | 7/2016 | Lee | |

OTHER PUBLICATIONS

Office Action in U.S. Appl. No. 13/555,965, dated Aug. 13, 2015, 9 pages.
Office Action in U.S. Appl. No. 13/392,387, dated Sep. 29, 2015, 9 pages.
Lane, "Differential double pulse voltammetry at chemically modified platinum electrodes for in vivo determination of catechol amines," Analytical Chemistry, 48(9)1287-1293, Aug. 1976.
Office action in U.S. Appl. No. 13/392,387, dated Jul. 13, 2016, 19 pages.
Office action in U.S. Appl. No. 13/555,965, dated Sep. 1, 2016, 10 pages.
International Preliminary Report on Patentability for PCT/US2014/050550, dated Feb. 18, 2016, 6 pages.
Abosch et al., "Stimulation of the subthalamic nucleus in Parkinson's disease does not produce striatal dopamine release," Neurosurgery, 2003, 53:1095-1102; discussion 1102-1095.
Adams, "In vivo electrochemical measurements in the CNS," Prog Neurobiol, 1990, 35(4):297-311.
Agnesi et al., "Wireless Instantaneous Neurotransmitter Concentration System-based amperometric detection of dopamine, adenosine, and glutamate for intraoperative neurochemical monitoring," J Neurosurg., 2009, 111:701-711.
Aillon et al., "Near real-time measurement of glutamate concentration changes using biosensors in place of traditional methodologies," in Phillips PEM, Sandberg SG, Ahn S, Phillips AG (ed): proceeding of the 12th international conference on in vivo methods 2008. University of British Columbia, Vancouver, Canada. 2008, pp. 108-110.

Albin et al., "The functional anatomy of basal ganglia disorders," Trends Neurosci., 1989, 12:366-375.
Anami et al., "Stepping stone sampling for retrieving artifactfree electroencephalogram during functional magnetic resonance imaging," Neuroimage, 2003, 19:281-295.
Anastassiou et al. "Subsecond voltammetric separation between dopamine and serotonin in the presence of ascorbate," Anal Chem., 78(19):6990-6998, Oct. 1, 2006.
Anderson et al., "Mechanisms of deep brain stimulation: an intracellular study in rat thalamus," J Physiol., 2004 559:301-313.
Bakker and Qin, "Electrochemical sensors," Anal Chem., 2006, 78:3965-3984.
Bar-Gad et al., "Complex locking rather than complete cessation of neuronal activity in the globus pallidus of a 1-methyl-4-phenyl-1,2,3,6-tetrahydropyridine-treated primate in response to pallidal microstimulation," J Neurosci., 2004, 24:7410-7419.
Bath et al., "Subsecond Adsorption and Desorption of Dopamine at Carbon-Fiber Microelectrodes," Anal. Chem., 2000, 72:5994-6002.
Baur et al., "Fast-scan voltammetry of biogenic amines," Anal Chem., 1988, 60:1268-1272.
Bekar et al., "Adenosine is crucial for deep brain stimulation-mediated attenuation of tremor," Nat Med., 2008, 14:75-80.
Benabid et al., "Combined (thalamotomy and stimulation) stereotactic surgery of the VIM thalamic nucleus for bilateral Parkinson disease," Appl Neurophysiol., 1987, 50:344-346.
Benabid, "Deep brain stimulation for Parkinson's disease," Curr Opin Neurobiol., 2003, 13:696-706.
Benveniste, "Brain microdialysis," J Neurochem., 1989, 52:1667-1679.
Bergman et al., "Pathophysiology of Parkinson's disease: from clinical neurology to basic neuroscience and back," Mov. Disord., 2002, 17:S28-S40.
Bergman et al., "Reversal of experimental parkinsonism by lesions of the subthalamic nucleus," Science, 1990, 249:1436-1438.
Bergstrom and Garris, "Utility of a tripolar stimulating electrode for eliciting dopamine release in the rat striatum," J Neurosci. Methods, 1999, 87:201-208.
Beurrier et al., "High-frequency stimulation produces a transient blockade of voltage-gated currents in subthalamic neurons," J Neurophysiol., 2001, 85:1351-1356.
Blagoev et al., "Modelling the magnetic signature of neuronal tissue," NeuroImage, 2007, 37:137-148.
Blaha and Phillips, "A critical assessment of electrochemical procedures applied to the measurement of dopamine and its metabolites during drug-induced and species-typical behaviours," Behav Pharmacol., 1996, 7:675-708.
Blaha and Winn, "Modulation of dopamine efflux in the striatum following cholinergic stimulation of the substantia nigra in intact and pedunculopontine tegmental nucleus-lesioned rats," J. Neurosci., 1993, 13(3):1035-1044.
Blaha et al., "Modulation of Dopamine Efflux in the Nucleus Accumbens after Cholinergic Stimulation of the Ventral Tegmental Area in Intact, Pedunculopontine Tegmental Nucleus-Lesioned, and Laterodorsal Tegmental Nucleus-Lesioned Rats," J. Neurosci., 1996, 16:714-722.
Blaha et al., "Striatal dopamine release evoked by subthalamic stimulation in intact and 6-0HDA-lesioned rats: Relevance to deep brain stimulation in Parkinson's Disease," In: P. E. M. Phillips, S. G. Sandberg, S. Ahn, A. G. Phillips (Eds.), Monitoring Molecules in Neuroscience. University of British Columbia, Vancouver, BC, 2008, pp. 395-397.
Bledsoe et al., "Development of the Wireless Instantaneous Neurotransmitter Concentration System for intraoperative neurochemical monitoring using fast-scan cyclic voltammetry," J Neurosurg., 2009, 111(4):712-723.
Bledsoe et al., "MRI compatible stereotaxic head-frame and navigation software for research in pigs," Neuroscience, 2008, Program#/Poster#: 695.8/UU92, 2 pages.
Bonmassar et al., "Visual evoked potential (VEP) measured by simultaneous 64-channel EEG and 3T fMRI," Neuroreport, 1999, 10:1893-1897.

(56) References Cited

OTHER PUBLICATIONS

Borland and Michael, "An introduction to electrochemical methods in neuroscience," in Michael AC, Borland LM (ed): Electrochemical Methods for Neuroscience. Boca Raton: CRC Press, 2007, 10 pages.
Borland et al., "Voltammetric study of extracellular dopamine near microdialysis probes acutely implanted in the striatum of the anesthetized rat," *J Neurosci Methods*, 2005, 146:149-158.
Breit et al., "Deep brain stimulation," *Cell Tissue Res*, 2004, 318:275-288.
Brown and Pilitsis, "Motor cortex stimulation for central and neuropathic facial pain: a prospective study of 10 patients and observations of enhanced sensory and motor function during stimulation," *Neurosurg.*, 2005, 56:290-297; discussion 290-297.
Bruet et al., "High frequency stimulation of the subthalamic nucleus increases the extracellular contents of striatal dopamine in normal and partially dopaminergic denervated rats," *J Neuropathol Exp Neurol.*, 2001, 60:15-24.
Bruet et al., "Neurochemical mechanisms induced by high frequency stimulation of the subthalamic nucleus: increase of extracellular striatal glutamate and GABA in normal and hemiparkinsonian rats," *J Neuropathol Exp Neurol.*, 2003, 62:1228-1240.
Burmeister et al., "Advances in the in vivo detection of GABA using enzyme coated microelectrode arrays," in Phillips PEM, Sandberg SG, Ahn S, Phillips AG (ed): proceeding of the 12th international conference on In Vivo methods 2008. University of British Columbia, Vancouver, Canada. 2008, p. 111-113.
Burmeister et al., "Improved ceramic-based multisite microelectrode for rapid measurements of L-glutamate in the CNS," *J Neurosci Methods*, 2002, 119:163-171.
Busenbark et al., "Accuracy of reported family histories of essential tremor," *Neurology*, 1996, 47:264-265.
Cahill et al., "Microelectrodes for the measurement of catecholamines in biological systems," *Anal Chem.*, 1996, 68(18):3180-3186.
Carmichael et al., "Functional MRI with active, fully implanted, deep brain stimulation systems: Safety and experimental confounds," *NeuroImage*, 2007, 37:508-517.
Cavus et al., "Decreased hippocampal volume on MRI is associated with increased extracellular glutamate in epilepsy patients," *Epilepsia*, 2008, 49:1358-1366.
Cechova and Venton, "Transient adenosine efflux in the rat caudate-putamen," *J Neurochem.*, 2008, 105:1253-1263.
Chang et al., "Studies of the neural mechanisms of deep brain stimulation in rodent models of Parkinson's disease," *Neurosci Biobehav Rev.*, 2008, 32:352-366.
Chow et al., "Delay in vesicle fusion revealed by electrochemical monitoring of single secretory events in adrenal chromaffin cells," *Nature*, 1992, 356(6364):60-63.
Clapp-Lilly et al., "An ultrastructural analysis of tissue surrounding a microdialysis probe," *J Neurosci Methods*, 1999, 90:129-142.
Covey et al., "Monitoring subthalamic nucleus-evoked dopamine release in the striatum using fast-scan cyclic voltammetry in vivo," in P.E.M. Phillips (Eds), Monitoring Molecules in Neuroscience. University of British Columbia, Vancouver, BC, 2008, 398-400.
Crespi et al., "In vivo voltammetry: from wire to wireless measurements," *J Neurosci Methods*, 2004, 140(1-2):153-61.
Cumming et al., "Kinetics of the uptake and distribution of the dopamine D(2,3) agonist (R)-N-[1-(11)C]n-propylnorapomorphine in brain of healthy and MPTP-treated Gottingen miniature pigs," *Nucl Med Biol.*, 2003, 30:547-553.
Dale et al., "Listening to the brain: microelectrode biosensors for neurochemicals," *Trends Biotechnol.*, 2005, 23:420-428.
Dale et al., "Rapid adenosine release in the nucleus tractus solitarii during defense response in rats: real-time measurement in vivo," *J Physiol.*, 2002, 544(Pt 1):149-160.
Dall et al., "Quantitative [18F]fluorodopa/PET and histology of fetal mesencephalic dopaminergic grafts to the striatum of MPTP-poisoned minipigs," *Cell Transplant.*, 2002, 11:733-746.
Danielsen et al., "The DaNeX study of embryonic mesencephalic, dopaminergic tissue grafted to a minipig model of Parkinson's disease: preliminary findings of effect of MPTP poisoning on striatal dopaminergic markers," *Cell Transplant.*, 2000, 9:247-259.
Dobbing, "The influence of early nutrition on the development and myelination of the brain," *Proc Royal Soc Lond B Biol Sci.*, 1964, 159:503-509.
Dommett et al., "How visual stimuli activate dopaminergic neurons at short latency," *Science*, 2005, 307:1476-1479.
Dostrovsky et al., "Microstimulation-induced inhibition of neuronal firing in human globus pallidus," *J Neurophysiol.*, 2000, 84:570-574.
Dugast et al., "Continuous in vivo monitoring of evoked dopamine release in the rat nucleus accumbens by amperometry," *Neuroscience*, 1994, 62:647-654.
Dunn et al., "Functional Brian Mapping at 9.4T Using a New MRI-Compatible Electrode Chronically Implanted in Rats," *Magnetic Resonance Med.*, 2009, 61:222-228.
Fedele et al., "Microdialysis in Parkinsonian patient basal ganglia: acute apomorphine-induced clinical and electrophysiological effects not paralleled by changes in the release of neuroactive amino acids," *Exp Neurol.*, 2001, 167:356-365.
Felix et al., "Stereotaxic atlas of the pig brain," *Brain Res Bull.*, 1999, 49:1-137.
Forster and Blaha, "Pedunculopontine tegmental stimulation evokes striatal dopamine efflux by activation of acetylocholine and glutamate receptors in the midbrain and pons of the rat," *Eur. J. Neurosci.*, 2003, 17:751-762
Frank et al., "Hold your horses: impulsivity, deep brain stimulation, and medication in parkinsonism," *Science*, 2007, 318:1309-1312.
Garcia et al., "Dual effect of high-frequency stimulation on subthalamic neuron activity," *J Neurosci.*, 2003, 23:8743-8751.
Garcia et al., "High-frequency stimulation in Parkinson's disease: more or less?" *Trends Neurosci.*, 2005, 28:209-216.
Garguilo and Michael, "Amperometric microsensors for monitoring choline in the extracellular fluid of brain," *J Neurosci Methods*, 1996, 70:73-82.
Garris et al., "Dissociation of dopamine release in the nucleus accumbens from intracranial self-stimulation," *Nature*, 1999, 398(6722):67-9.
Garris et al., "Dopamine release and uptake both decrease in the partially denervated striatum in proportion to the loss of dopamine terminals," *Brain Res.*, 1997, 753(2):225-34.
Garris et al., "In vivo voltammetry with telemetry," in Michael AC, Borland LM (ed): Electrochemical Methods for Neuroscience. Boca Rhaton: CRC Press, 2007, pp. 233-259.
Garris et al., "Real-time measurement of electrically evoked extracellular dopamine in the striatum of freely moving rats," *J Neurochem.*, 1997, 68:152-161.
Garris et al., "Wireless transmission of fast-scan cyclic voltammetry at a carbon-fiber microelectrode: proof of principle," *J Neurosci Methods*, 2004, 140(1-2):103-115.
Gerhardt, "Rapid chronocoulometric measurements of norepinephrine overflow and clearance in CNS tissues," Neuromethods: voltammetric methods in brain systems, ed. G.B. A Boulton, RN Adams. 1995, Totowa, NJ: Human Press Inc. 117-51.
Gourine et al., "Adenosine release in nucleus tractus solitarii does not appear to mediate hypoxia-induced respiratory depression in rats," *J Physiol.*, 2002, 544:161-70.
Graybiel, "Neurotransmitters and neuromodulators in the basal ganglia," *Trends Neurosci*, 1990, 13:244-254.
Greene, "Deep-brain stimulation for generalized dystonia," *N Engl J Med*, 2005, 352:498-500.
Groh and Ney, "Anesthesia for magnetic resonance imaging," *Curr Opin Anaethesiol.*, 1997, 10:303-308.
Halassa et al., "Astrocytic Modulation of Sleep Homeostasis and Cognitive Consequences of Sleep Loss," *Neuron*, 2009, 61:213-219.
Hardesty and Sackeim, "Deep brain stimulation in movement and psychiatric disorders," *Biol Psychiatry*, 2007, 61:831-835.
Hardman et al., "Comparison of the Basal Ganglia in Rats, Marmosets, Macaques, Baboons, and Humans: Volume and Neuronal (56) References Cited

OTHER PUBLICATIONS

Number for the Output, Internal Relay and Striatal Modulating Nuclei," *J Comp. Neural.*, 2002, 445:238-255.

Hascup et al., "Determining the source of resting and physiologically-evoked L-glutamate levels using enzyme-based microelectrode arrays in awake rats," in Phillips PEM, Sandberg SG, Ahn S, Phillips AG (ed): proceeding of the 12th international conference on in vivo methods 2008. University of British Columbia, Vancouver, Canada. 2008, pp. 164-167.

Hascup et al., "Second-by second measures of L-glutamate and other neurotransmitter using enzyme based microelectrode arrays," in Micheal AC, Borland LM (ed): Electrochemical methods for neuroscience. CRC. 2006, 47 pages.

Henderson and Lad, "Motor cortex stimulation and neuropathic facial pain," *Neurosurg Focus*, 2006, 21:E6, 4 pages.

Herzog et al., "Most effective stimulation site in subthalamic deep brain stimulation for Parkinson's disease," *Mov. Disord.*, 2004, 19:1050-1054.

Hilker et al., "Deep brain stimulation of the subthalamic nucleus does not increase the striatal dopamine concentration in parkinsonian humans," *Mov Disord*, 2003, 18:41-48.

Hinzman et al., "Alterations in glutamate neurotransmission after traumatic brain injury: Study using enzyme-based microelectrode arrays," in Phillips PEM, Sandberg SG, Ahn S, Phillips AG (ed): proceeding of the 12th international conference on in vivo methods 2008. University of British Columbia, Vancouver, Canada. 2008, p. 372-374.

Hubble et al., "Deep brain stimulation for essential tremor," *Neurol.*, 1996, 46:1150-1153.

Huffman and Venton, "Carbon-fiber microelectrodes for in vivo applications," *Analyst.*, 2009, 134:18-24.

Hurley et al., "What has been learnt from study of dopamine receptors in Parkinson's disease?" *Pharmacol. Ther.*, 2002, 111:715-728.

Hyland et al., "Firing modes of midbrain dopamine cells in the freely moving rat," *Neurosci.*, 2002, 114:475-492.

Jackson et al., "Fast-scan cyclic voltammetry of 5-hydroxytryptamine," *Anal Chem.*, 1995, 67:1115-1120.

Jang et al. "Paired pulse voltammetry for differentiating complex analytes," *Analyst.* 137(6):1428-1435, Epub Feb. 2, 2012.

Jaquins-Gerstl and Michael, "Comparison of the brain penetration injury associated with microdialysis and voltammetry," *J Neurosci Methods*, 2009, 183:127-135.

Justice et al., "Voltammetry in the neuroscience," Clifton, NJ. Humana Press, 1987, 395 pages.

Kagohashi et al., "Wireless voltammetry recording in unanesthetised behaving rats," *Neurosci Res.*, 2008, 60:120-127.

Kawagoe et al., "pH-Dependent processes at Nation-coated carbon-fiber microelectrodes," *J Electroanal Chem.*, 1993, 359:193-197.

Keeler et al., "Accessory equipment considerations with respect to MRI compatibility," *J Magn Reson Imaging*, 1998, 8:12-18.

Kern and Kumar, "Deep brain stimulation," *Neurologist*, 2007, 13:237-252.

Kimble et al., "Wireless Instantaneous Neurotransmitter Concentration Sensing System (WINCS) for Intraoperative Neurochemical Monitoring," *31st Annual International Conference of the IEEE EMBS*, 2009, 4 pages.

Kita and Kitai, "Efferent Projections of the Subthalamic Nucleus in the Rat: Light and Electron Microscopic Analysis with the PHA-L Method," *J Comp. Neural.*, 1987, 260:435-452.

Konradsson et al., "Second-by-second measurement of stimulated glutamate release and its modulation by α7 and mGlu 2/3 receptors: relevance to schizophrenia," in Phillips PEM, Sandberg SG, Ahn S, Phillips AG (ed): proceeding of the 12th international conference on in vivo methods 2008. University of British Columbia, Vancouver, Canada. 2008, pp. 123-126.

Krakow, "Imaging epileptic activity using functional MRI," *Neurodegener Dis*, 2008, 5:286-295.

Kristensen and Wightman, "Dispersion in flow injection analysis measured with microvoltammetric electrodes," *Anal Chem*, 1986, 58:986-988.

Kulagina et al., "Monitoring glutamate and ascorbate in the extracellular space of brain tissue with electrochemical microsensors," *Anal Chem.*, 1999, 71:5093-5100.

Lee et al, "Evolution of Deep Brain Stimulation: Human Electrometer and Smart Devices Supporting the Next Generation of Therapy," *Neuromodulation: Technology at the Neural Interface*, 2009, 12(2):85-103.

Lee et al., "Dopamine efflux in the rat striatum evoked by electrical stimulation of the subthalamic nucleus: potential mechanism of action in Parkinson's disease," *Eur. J. Neurosci.*, 2006, 23:1005-1014.

Lee et al., "Effect of High-Frequency Stimulation of the Subthalamic Nucleus on Subthalamic Neurons: An Intracellular Study," *Stereotactic. Funct. Neurasurg.*, 2003, 80:32-36.

Lee et al., "High-frequency stimulation of the subthalamic nucleus increases glutamate in the subthalamic nucleus of rats as demonstrated by in vivo enzyme-linked glutamate sensor," *Brain Res.*, 2007, 1162:121-129.

Lee et al., "Neurotransmitter release from high-frequency stimulation of the subthalamic nucleus," *J Neurosurg.*, 2004, 101:511-517.

Limberger et al., "'Real time' measurement of endogenous dopamine release during short trains of pulses in slices of rat neostriatum and nucleus accumbens: role of autoinhibition," *Naunyn-Schmiedeberg's Arch Pharmacol.*, 1991, 344:623-629.

Limousin et al., "Electrical stimulation of the subthalamic nucleus in advanced Parkinson's disease," *N Engl J Med*, 1998, 339:1105-1111.

Lind et al., "Mapping the amphetamine-evoked dopamine release in the brain of the Göttingen minipig," *Brain Res Bull.*, 2005, 65:1-9.

Lind et al., "The use of pigs in neuroscience: modeling brain disorders," *Neurosci Biobehav Rev,* 2007, 31(5):728-51.

Littlewood et al., "Mapping the central effects of ketamine in the rat using pharmacological MRI," *Psychopharmacology* (Berl), 2006, 186:64-81.

Llaudet et al., "A three-enzyme microelectrode sensor for detecting purine release from central nervous system," *Biosens Bioelectron.*, 2003, 18:43-52.

Logothetis et al., "Neurophysiological investigation of the basis of the fMRI signal," *Nature,* 2001, 412:150-157.

Lowry and Fillenz, "Real-time monitoring of brain energy metabolism in vivo using microelectrochemical sensors: the effects of anesthesia," *Bioelectrochem.*, 2001, 54:39-47.

Lowry eta l., "An amperometric glucose-oxidase/poly(o-phenylenediamine) biosensor for monitoring brain extracellular glucose: in vivo characterization in the striatum of freely-moving rats," *J Neurosci Methods*, 1998, 79:65-74.

Lozano et al., "Subcallosal cingulate gyrus deep brain stimulation for treatment-resistant depression," *Biol Psychiatry,* 2008, 64:461-467.

Maarrawi et al., "Motor cortex stimulation for pain control induces changes in the endogenous opioid system," *Neurol.*, 2007, 69:827-834.

Macmillan et al., "Accuracy of a miniature intracranial pressure monitor, its function during magnetic resonance scanning, and assessment of image artifact generation," *Neurosurgery,* 1999, 45:188-192.

Mandelkow et al., "Synchronization facilitates removal of MRI artefacts from concurrent EEG recordings and increases usable bandwidth," *Neuroimage*, 2006, 32-1120-1126.

Mayberg et al., "Deep brain stimulation for treatment-resistant depression," *Neuron*, 2005, 45:651-660.

Mazzone et al., "Implantation of human pedunculopontine nucleus: a safe and clinically relevant target in Parkinson's disease," *Neuroreport*, 2005, 16:1877-1881.

McIntyre et al., "Uncovering the mechanism(s) of action of deep brain stimulation: activation, inhibition, or both," *Clin Neurophysiol.*, 2004, 115:1239-1248.

Meissner et al., "Deep brain stimulation in late stage Parkinson's disease: a retrospective cost analysis in Germany," *J Neurol.* 2005, 252:218-223.

(56) References Cited

OTHER PUBLICATIONS

Meissner et al., "Deep brain stimulation of subthalamic neurons increases striatal dopamine metabolism and induces contralateral circling in freely moving 6-hydroxydopamine-lesioned rats," *Neurosci Lett.*, 2002, 328:105-108.
Meissner et al., "Striatal dopaminergic metabolism is increased by deep brain stimulation of the subthalamic nucleus in 6-hydroxydopamine lesioned rats," *Neurosci Lett.*, 2001, 303:165-168.
Meltzer et al., "Modulation of dopamine neuronal activity by glutamate receptor subtypes," *Neurosci. Biobehav. Rev.*, 1997, 21:511-518.
Menon et al., "Combined event-related fMRI and EEG evidence for temporal-parietal cortex activation during target detection," *Neuroreport*, 1997, 8:3029-3037.
Michael et al., "Improving data acquisition for fast-scan cyclic voltammetry," *Anal Chem.*, 1999, 71(18):3941-3947.
Mikkelsen et al., "MPTP-induced Parkinsonism in minipigs: A behavioral, biochemical, and histological study," *Neurotoxicol Teratol*, 1999, 21(2):169-75.
Mitchell, "Acetylcholine and choline amperometric enzyme sensors characterized in vitro and in vivo," *Anal Chem.*, 2004, 76:1098-106.
Molina et al., "Additive Differential pulse voltammetry, instead of double differential pulse voltammetry," *Electrochem. Commun.*, 2001, 3:324-329.
Molinuevo et al., "Levodopa withdrawal after bilateral subthalamic nucleus stimulation in advanced Parkinson disease," *Arch Neurol.*, 2000, 57:983-988.
Moro et al., "Chronic subthalamic nucleus stimulation reduces medication requirements in Parkinson's disease," *Neurol.*, 1999, 53:85-90.
Moro et al., "The Impact on Parkinson's disease of electrical parameter settings in STN stimulation," *Neurology*, 2002, 59:706-713.
Moyer et al., "Effects of dopaminergic modulation on the integrative properties of the ventral striatal medium spiny neuron," *J Neurophysiol.*, 2007, 98:3731-3748.
Nandi et al., "Exploration of the role of the upper brainstem in motor control," *Stereotact Funct Neurosurg*, 2002, 78(3-4):158-167.
Naylor et al., "A new technique for the simultaneous recording of electroencephalograph activity and CNS biosensor data," in Phillips PEM, Sandberg SG, Ahn S, Phillips AG (ed): proceeding of the 12th international conference on in vivo methods 2008. University of British Columbia, Vancouver, Canada. 2008, pp. 127-129.
Netchiporouk et al., "Brain extracellular glucose assessed by voltammetry throughout the rat sleep-wake cycle," *Eur J Neurosci.*, 2001, 13:1429-1434.
Niazy et al., "Removal of FMRI environment artifacts from EEG data using optimal basis sets," *Neuroimage*, 2005, 28:720-737.
Nomoto et al., "The metabolic rate and vulnerability of dopaminergic neurons, and adenosine dynamics in the cerebral cortex, nucleus accumbens, caudate nucleus, and putamen of the common marmoset," *J Neural.*, 2000, 247:16-22.
Norris, "Principles of magnetic resonance assessment of brain function," *J Magn Reson Imaging*, 2006, 23:794-807.
Patel et al., "Unilateral subthalamotomy in the treatment of Parkinson's disease," *Brain*, 2003, 126:1136-1145.
Paul et al., "High frequency stimulation of the subthalamic nucleus influences striatal dopaminergic metabolism in the naive rat," *Neuroreport*, 2000, 11:441-444.
Perea and Araque, "Astrocytes potentiate transmitter release at single hippocampal synapses," *Science*, 2007, 317:1083-1086.
Phillips et al., "Parkinson disease: pattern of functional MR imaging activation during deep brain stimulation of subthalamic nucleus—initial experience," *Radiology*, 2006, 239:209-216.
Pohlmeyer et al., "Toward the Restoration of Hand Use to a Paralyzed Monkey: Brain-Controlled Functional Electrical Stimulation of Forearm Muscles," *PLoS ONE*, 2009, 4(6):1-8.
Pomerleau et al., "Real time in vivo measures of L-glutamate in the rat central nervous system using ceramic-based multisite microelectrode arrays," *Ann N Y Acad Sci.*, 2003, 1003:454-7.
Priori et al., "Do intraoperative microrecordings improve subthalamic nucleus targeting in stereotactic neurosurgery for Parkinson's disease?" *J Neurosurg Sci.*, 2003, 47:56-60.
Purdon et al., "An open-source hardware and software system for acquisition and real-time processing of electrophysiology during high field MRI," *J Neurosci Methods*, 2008, 175:165-186.
Purdon et al., "Simultaneous electroencephalography and functional magnetic resonance imaging of general anesthesia," *Ann N Y Acad Sci.*, 2009, 1157:61-70.
Rehncrona et al., "Long-term efficacy of thalamic deep brain stimulation for tremor: double-blind assessments," *Mov Disord.*, 2003, 18:163-170.
Ren et al., "Dopaminergic response to graded dopamine concentration elicited by four amphetamine doses," *Synapse*, 2009, 63:764-772.
Roberts and Mikulis, "Neuro MR: principles," *J Magn Reson Imaging*, 2007, 26:823-837.
Robinson et al., "Detecting Subsecond Dopamine Release with Fast-Scan Cyclic Voltammetry in Vivo," *Clin. Chem.*, 2003, 49:1763-1773.
Robinson et al., "Monitoring rapid chemical communication in the brain," *Chem Rev.*, 2008, 108:2554-2584.
Roham et al., "Diamond microelectrodes and CMOS microelectronics for wireless transmission of fast-scan cyclic voltammetry," *Conf Proc IEEE Eng Med Biol Soc*, 2007. 2007::6044-7.
Saint-Cyr et al., "Localization of clinically effective stimulating electrodes in the human subthalamic nucleus on magnetic resonance imaging," *J. Neurosurg.*, 2002, 97:1152-1166.
Sandberg and Garris, "Neurochemistry of addiction: monitoring essential neurotransmitters of addiction," in Koob GF, Kuhn C (ed): Novel Approaches to Addiction Boca Raton: CRC Press, 2010, 30 pages.
Saunders et al., "Microdialysis in nonhuman Primates," *Curr Protoc Neurosci*, 2001, Chapter 7:Unit7, 20 pages.
Schwarz et al., "Concurrent pharmacological MRI and in situ microdialysis of cocaine reveal relationship between the central hemodynamic response and local dopamine concentration," *Neuroimage*, 2004, 23:296-304.
Shastry, "Parkinson disease: etiology, pathogenesis and future of gene therapy," *Neurosci. Res.*, 2001, 41:5-12.
Shimo and Wichmann, "Neuronal activity in the subthalamic nucleus modulates the release of dopamine in the monkey striatum," *Eur. J Neurosci.*, 2009, 29:104-113.
Shon et al., "Comonitoring of adenosine and dopamine using the Wireless Instantaneous Neurotransmitter Concentration System: proof of principle: Laboratory investigation," *J Neurosurg.*, 2010, 112(3):539-548.
Stefurak et al., "Deep brain stimulation for Parkinson's disease dissociates mood and motor circuits: a functional MRI case study," *Mov Disord*, 2003, 18:1508-1516.
Suaud-Chagny et al., "Uptake of dopamine released by impulse flow in the rat mesolimbic and striatal systems in vivo," *J Neurochem.*, 1995, 65:2603-2611.
Suaud-Chagny, "In vivo monitoring of dopamine overflow in the central nervous system by amperometric techniques combined with carbon fibre electrodes," *Methods.*, 2004, 33:322-329.
Swamy et al., "Subsecond Detection of Physiological Adenosine Concentrations Using Fast-Scan Cyclic Voltammetry," *Anal. Chem.*, 2007, 79:744-750.
Tawfik et al., "Deep Brain Stimulation Results in Local Glutamate and Adenosine Release" Investigation into the Role of Astrocytes, *Neurosurgery*, 2010, 67:367-75.
Thobois et al., "Chronic subthalamic nucleus stimulation and striatal D2 dopamine receptors in Parkinson's disease—A [(11)C]-raclopride PET study," *J Neurol.*, 2003, 250:1219-1223.
Tsubokawa et al., "Chronic motor cortex stimulation for the treatment of central pain," *Acta Neurochir Suppl (Wien)*, 1991, 52:137-139.
Tsubokawa et al., "Chronic motor cortex stimulation in patients with thalamic pain," *J Neurosurg.*, 1993, 78:393-401.

(56) References Cited

OTHER PUBLICATIONS van der Zeyden et al., "Microdialysis of GABA and glutamate: analysis, interpretation and comparison with microsensors," *Pharmacol Biochem Behav.*, 2008, 90:135-147.

Venton et al., "Real-time decoding of dopamine concentration changes in the caudate-putamen during tonic and phasic firing," *J Neurochem*, 2003, 87:1284-1295.

Voges et al., "Bilateral high-frequency stimulation in the subthalamic nucleus for the treatment of Parkinson disease: correlation of therapeutic effect with anatomical electrode position," *J. Neurosurg.*, 2002, 96:269-279.

Volkmann, "Deep brain stimulation for the treatment of Parkinson's disease," *J Clin Neurophysiol.*, 2004, 21:6-17.

Watson et al., "In vivo measurements of neurotransmitters by microdialysis sampling," *Anal Chem*, 2006, 78:1391-1399.

Welter et al., "Effects of high-frequency stimulation on subthalamic neuronal activity in parkinsonian patients," *Arch Neurol.*, 2004, 61:89-96.

Wiedemann et al., "Strategies for Low Detection Limit Measurements with Cyclic Voltammetry," *Anal. Chem.*, 1991, 63:2965-2970.

Wightman et al., "Temporally resolved catecholamine spikes correspond to single vesicle release from individual chromaffin cells," *Proc Natl Acad Sci USA*, 1991, 88:10754-10758.

Williams and Millar, "Concentration-dependent actions of stimulated dopamine release on neuronal activity in rat striatum," *Neuroscience*, 1990, 39(1):1-16.

Williams and Millar, "Differential Actions of Endogenous and Iontophoretic Dopamine in Rat Striatum," *Eur J Neurosci*, 1990, 2(7):658-661.

Wilson and Gifford, "Biosensors for real-time in vivo measurements," *Biosens Bioelectron.*, 2005, 20:2388-2403.

Windels et al., "Effects of high frequency stimulation of subthalamic nucleus on extracellular glutamate and GABA in substantia nigra and globus pallidus in the normal rat," *Eur J Neurosci.*, 2000, 12:4141-4146.

Wu et al., "Determination of release and uptake parameters from electrically evoked dopamine dynamics measured by real-time voltammetry," *J Neurosci Methods*, 2001, 112:119-133.

Zhao et al., "Long term high frequency stimulation of STN increases dopamine in the corpus striatum of hemiparkinsonian rhesus monkey," *Brain Res.*, 2009, 1286:230-238.

Office Action in U.S. Appl. No. 13/555,965, dated Feb. 12, 2015, 8 pages.

U.S. Appl. No. 61/358,512, filed Jun. 25, 2010, 51 pages.

International Preliminary Report on Patentability in International Application No. PCT/US2010/046807, dated Mar. 8, 2012, 6 pages.

International Search Report and Written Opinion for PCT/US2014/10882, dated Apr. 4, 2014, 12 pages.

International Search Report and Written Opinion for PCT/US2014/50550 dated Nov. 20, 2014, 10 pages.

International Search Report and Written Opinion in International Application No. PCT/US2010/046807, dated May 31, 2011, 9 pages.

* cited by examiner

Figure 5E

SYSTEMS FOR THE DETECTION AND DELIVERY OF NEUROCHEMICAL AND ELECTRICAL SIGNALS FOR FUNCTIONAL RESTORATION

CROSS-REFERENCE TO RELATED APPLICATIONS

This application is a National Stage application under 35 U.S.C. § 371 of International Application No. PCT/US2014/010882, filed Jan. 9, 2014, which claims the benefit of U.S. Provisional Application Ser. No. 61/750,550, filed Jan. 9, 2013. The disclosure of the prior application is considered part of (and is incorporated by reference in) the disclosure of this application.

BACKGROUND

1. Technical Field

This document relates to methods and materials involved in detecting and delivering neurochemical signals, electrophysiological signals, ions, or combinations thereof within a mammal. For example, this document relates to methods and materials for using an implantable device containing probes to detect neurochemical signals (e.g., neurotransmitter concentrations), electrical signals, ions, or combinations thereof within one region of a mammal's brain and an implantable device containing electrodes and microfluidic delivery components to deliver neurochemical signals (e.g., neurotransmitters), electrical signals, ions, or combinations thereof to another location within the mammal (e.g., in the brain, spinal cord region, peripheral nervous system, or a muscle region within a mammal).

2. Background Information

The brain, spinal cord, and peripheral nervous system use electrical and chemical signaling to control movements and processes within a mammal. In some cases, artificial electrical stimulation can be performed within a mammal's brain to treat certain conditions. For example, deep brain stimulation (DBS) surgery, a neurosurgical intervention procedure, can be used to treat single or multiple disorders, including Parkinson's disease (PD), tremor, dystonia, depression, and chronic pain. Several theories have been proposed to account for the therapeutic action of DBS, some of which are based on the stimulation evoked release of neurotransmitters such as dopamine, glutamate, GABA, and adenosine from proximal and distal brain nuclei.

SUMMARY

This document provides methods and materials involved in detecting and delivering neurochemical signals, electrophysiological signals, ions, or combinations thereof within a mammal. For example, this document provides systems that can include one or more implantable devices containing probes configured to detect neurochemical signals (e.g., neurotransmitter concentrations), electrical signals, ions, or combinations thereof and one or more implantable devices containing electrodes and/or microfluidic delivery components configured to deliver neurochemical signals (e.g., neurotransmitters), electrical signals, ions, or combinations thereof to one or more locations within a mammal.

As described herein, a system provided herein can include an implantable detection device configured to be implanted into a first location within the brain of a mammal. Such an implantable detection device can include one or more probes configured to detect neurochemical signals (e.g., neurotransmitter concentrations), electrical signals, ions, or combinations thereof and can be configured to send information about detected neurochemical signals, electrical signals, and ions. The system also can include an implantable delivery and detection device configured to be implanted into a location outside of the brain of the mammal. For example, an implantable delivery and detection device can be configured to be implanted within a spinal cord region of a mammal with a damaged or severed spinal cord such that the delivery and detection device is located downstream of the damaged or severed spinal cord. Such an implantable delivery and detection device can include one or more electrodes for delivering electrical signals to the mammal's tissue (e.g., nerves or muscle tissue), one or more microfluidic components for delivering chemical signals and/or ions to the mammal's tissue (e.g., nerves or muscle tissue), and one or more probes configured to detect neurochemical signals (e.g., neurotransmitter concentrations), electrical signals, ions, or combinations thereof. Such an implantable delivery and detection device also can be configured to receive information about detected neurochemical signals, electrical signals, and ions sent from the detection device located in the brain and can be configured to send information about detected neurochemical signals, electrical signals, and ions in the region of the delivery and detection device.

Having the ability to detect neurochemical signals, electrical signals, ions, or combinations thereof in one location within a mammal's brain quickly and accurately and to deliver neurochemical signals, electrical signals, ions, or combinations thereof to another location within the mammal's body that is downstream of a damaged or severed nerve (e.g., spinal cord injury) quickly and accurately in response to the detected signals can allow researchers, medical personnel, and patients to reconnect communication across a damaged or severed nerve. Such reconnected communication can allow different combinations of signals to be assessed for the ability to activate particular muscular movements downstream of a damaged or severed nerve in response to a particular detected signal profile within a region of the brain. In some cases, the systems provided herein can be used to create a list of brain signal profiles that represent particular desired or needed muscular movements and a list of delivery signal profiles that have the ability to activate particular muscular movements.

In general, one aspect of this document features a system for detecting signals within the brain of a mammal and delivering signals to nerve tissue downstream of a damaged or severed nerve. The system comprises, or consists essentially of, (a) a first implantable device comprising one or more probes configured to detect neurochemical and electrical signals within a first region of the brain, (b) a second implantable device comprising one or more electrodes configured to deliver electrical signals to the nerve tissue, and (c) a third implantable device comprising one or more electrodes configured to deliver electrical signals to a second region of the brain or one or more microfluidic delivery components configured to deliver neurochemical signals to the second region of the brain, wherein the first implantable device is configured to send information about detected neurochemical and electrical signals directly or indirectly to the second implantable device, wherein the second implantable device is configured to deliver electrical signals and neurochemical signals to the nerve tissue based on the information, and wherein the third implantable device is configured to deliver electrical signals or neurochemical signals to the second region of the brain while or after the second implantable device is delivering electrical signals and neurochemical signals to the nerve tissue. The second implantable device can comprise one or more microfluidic delivery components configured to deliver neurochemical signals to the nerve tissue. The second implantable device can be located within a limb, a diaphragm, a genital region, a bladder, a vascular system, or facial tissue.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides methods and materials involved in detecting and delivering neurochemical signals, electrical signals, ions, or combinations thereof within a mammal. For example, this document provides systems that can include one or more implantable devices containing probes configured to detect neurochemical signals (e.g., neurotransmitter concentrations), electrical signals, ions, or combinations thereof and one or more implantable devices containing electrodes and/or microfluidic delivery components configured to deliver neurochemical signals (e.g., neurotransmitters), electrical signals, ions, or combinations thereof to one or more locations within a mammal. In some cases, an implantable device containing a probe can include one or more transmitters and/or one or more processors configured to transmit wirelessly information or instructions about the detected signals to an implantable device containing an electrode and/or microfluidic delivery components. In some cases, an implantable device containing an electrode and/or microfluidic delivery components can include one or more receivers and/or one or more processors configured to receive information or instructions sent from an implantable device containing a probe. The methods and materials provided herein can be used with any appropriate mammal including, without limitation, humans, monkeys, horses, cows, pigs, sheep, goats, dogs, cats, rabbits, rats, and mice.

In some cases, an implantable device containing one or more probes configured to detect neurochemical signals, electrical signals, ions, or combinations thereof can be implanted into a region of a mammal's brain to detect neurochemical signals, electrical signals, ions, or combinations thereof within that region. Examples of neurochemicals that can be detected using the methods and materials provided herein include, without limitation, dopamine, serotonin, adenosine, adenine mono- or tri-phosphate, norepinephrine, GABA, histamine, acetylcholine, glutamate, aspartate, epinephrine, nitric oxide, glycine, trace amines (e.g., tryptamine, phenylethylamine, tyramine, and octopamine), and amino acid-based neuropeptides (e.g., endorphins, enkephalins, and vasopressin). For example, an implantable device containing one or more probes provided herein can include one or more sensors to detect one or more neurochemicals. In some cases, a single sensor can be used to detect a single neurochemical. For example, an implantable device containing one or more probes provided herein can include a first sensor designed to detect dopamine and a second sensor designed to detect glutamate. Another design is to use a singular sensing electrode, and by impressing different voltage ramps, different neurochemicals can be detected using the same sensing electrode at slightly different times.

The methods and materials provided herein can be used to detect any appropriate electrical signal generated within a mammal (e.g., a human). For example, an implantable device containing one or more probes provided herein can include one or more sensors to detect electrical signals within the brain of a mammal.

Examples of ions that can be detected using the methods and materials provided herein include, without limitation, calcium, magnesium, sodium, potassium, protons (pH), iron, copper, chromium, lead, mercury, cobalt, gold, lithium, cesium, barium, zinc, chloride, bicarbonate, phosphate, bromide, iodide, sulfide, oxide, sulfide, oxygen, and fluoride. For example, an implantable device containing one or more probes provided herein can include one or more sensors to detect one or more ions. In some cases, a single sensor can be used to detect a single ion. For example, an implantable device containing one or more probes provided herein can include a first sensor designed to detect calcium and a second sensor designed to detect protons. Another design is to use a singular sensing electrode, and by impressing different voltage ramps, different ions can be detected using the same sensing electrode at slightly different times.

An implantable device containing one or more probes configured to detect neurochemical signals, electrical signals, ions, or combinations thereof can be implanted into any appropriate region of a mammal's brain to detect neurochemical signals, electrical signals, ions, or combinations thereof within that region. For example, an implantable device containing one or more probes configured to detect neurochemical signals, electrical signals, ions, or combinations thereof can be implanted into the cerebral cortex, thalamus, basal ganglia, or brainstem region of a mammal's brain.

In some cases, an implantable device containing one or more probes configured to detect neurochemical signals, electrical signals, ions, or combinations thereof can be configured to send the detected information regarding neurochemical signals, electrical signals, ions, or combinations thereof to a control unit located within or outside of the mammal. For example, an implantable device containing one or more probes can be configured to send the detected information to a computerized control unit having the ability to assess the information for particular signal profiles. In such cases, the computerized control unit can send information about the detected information or about a particular signal profile to one or more other implanted devices (e.g., an implantable devices containing electrodes and/or microfluidic delivery components configured to deliver neurochemical signals, electrical signals, ions, or combinations thereof to one or more locations within the mammal). In some cases, an implantable device containing one or more probes configured to detect neurochemical signals, electrical signals, ions, or combinations thereof can be configured to include a computerized control unit capable of sending information about the detected information or about a particular signal profile to one or more other implanted devices.

In general, an implantable device containing one or more probes configured to detect neurochemical signals, electrical signals, ions, or combinations thereof is used in combination with one or more implantable devices containing one or more electrodes and/or microfluidic delivery components configured to deliver neurochemical signals, electrical signals, ions, or combinations thereof. In some cases, an implantable device containing one or more electrodes and/or microfluidic delivery components configured to deliver neurochemical signals, electrical signals, ions, or combinations thereof can be implanted within a mammal's body to deliver neurochemical signals, electrical signals, ions, or combinations thereof to that region of the mammal's body. Such an implantable device containing one or more electrodes and/or microfluidic delivery components configured to deliver neurochemical signals, electrical signals, ions, or combinations thereof can be configure to receive signals from a computerized control unit capable of sending information. Such information can include, without limitation, information about detected information obtained from an implantable device containing one or more probes configured to detect neurochemical signals, electrical signals, ions, or combinations thereof, information about a particular signal profile obtained from an implantable device containing one or more probes configured to detect neurochemical signals, electrical signals, ions, or combinations thereof, or information about the type and/or duration of signals to deliver. For example, an implantable device containing one or more probes configured to detect neurochemical signals, electrical signals, ions, or combinations thereof can include a computerized control unit that sends a delivery signal profile based on detected information about neurochemical signals, electrical signals, and/or ions within the brain of a mammal to an implantable device containing one or more electrodes and/or microfluidic delivery components configured to deliver neurochemical signals, electrical signals, and/or ions to the mammal. Once such information is received by an implantable device containing one or more electrodes and/or microfluidic delivery components configured to deliver neurochemical signals, electrical signals, and/or ions, that implantable device can deliver neurochemical signals, electrical signals, and/or ions to the mammal according to the information received.

An implantable device containing one or more electrodes and/or microfluidic delivery components configured to deliver neurochemical signals, electrical signals, and/or ions can be implanted into any appropriate region of a mammal's body to deliver neurochemical signals, electrical signals, ions, or combinations thereof to that region. For example, an implantable device containing one or more electrodes and/or microfluidic delivery components can be implanted a region such as the spinal cord region, a dorsal root ganglia, a peripheral nerve, or a muscle such as the diaphragm, bladder, or the like. In some cases, an implantable device containing one or more electrodes and/or microfluidic delivery components can be implanted downstream of a damaged or severed nerve (e.g., damaged or severed spinal cord).

Any appropriate electrical signal can be delivered to a mammal's tissue (e.g., nerve tissue or muscle tissue) when an implanted device containing one or more electrodes and/or microfluidic delivery components is triggered to deliver an electrical signal. For example, continuous electrical stimulation, electrical pulses, sigmoidal pulses, or any user defined pulses can be delivered by an implantable device containing one or more electrodes and optionally one or more microfluidic delivery components.

Any appropriate neurochemical signal or ion can be delivered to a mammal's tissue (e.g., nerve tissue or muscle tissue) when an implanted device containing one or more electrodes and/or microfluidic delivery components is triggered to deliver a neurochemical signal or ion. For example, adenosine, serotonin, norepinephrine, and/or protons can be delivered by an implantable device containing one or more microfluidic delivery components and optionally one or more electrodes. In some cases, an implantable device containing one or more microfluidic delivery components and optionally one or more electrodes can be configured to deliver growth factors such as nerve growth factor, glia derived neurotrophic factor, or epidermal growth factor. For example, growth factors can be delivered to a particular location within a mammal in addition electrical signals, neurochemical signals, and ions.

In some cases, an implantable device containing one or more electrodes and/or microfluidic delivery components configured to deliver neurochemical signals, electrical signals, and/or ions can include one or more probes configured to detect neurochemical signals, electrical signals, ions, or combinations thereof. In such cases, the implantable device can be configured to send the detected information regarding neurochemical signals, electrical signals, ions, or combinations thereof to a control unit located within or outside of the mammal. For example, an implantable device configured to deliver and to detect signals can be configured to send the detected information to a computerized control unit having the ability to assess the information for particular signal profiles. In such cases, the computerized control unit can send information about the detected information or about a particular signal profile to one or more other implanted devices (e.g., a first implantable device containing one or more probes that is located within a first location within the mammal's brain or a second implantable device containing one or more probes that is located within a second location within the mammal's brain). In some cases, an implantable device configured to deliver and to detect signals can be configured to include a computerized control unit capable of sending information about the detected information or about a particular signal profile to one or more other implanted devices.

In some cases, three or more implantable device can be used in combination to create a feedback system. For example, a first implantable device containing one or more probes can be positioned at a first location within the mammal's brain to obtain a first signal profile. Once detected, the signal profile or information about the signals to be delivered based on that signal profile can be sent to a second implantable device containing one or more electrodes and/or one or more microfluidic delivery components that is positioned at a second location within the mammal's body. In some cases, the second location can be a region downstream of a damaged or severed nerve (e.g., a region proximal to a severed nerve). Such a second implantable device can be configured to deliver electrical signals, neurochemical signals, growth factors, and/or ions based on the information received from the first implantable device or a computerized control unit in communication with the first implantable device. In some cases, the second implantable device can be configured to detect electrical signals, neurochemical signals, and/or ions within the region where it is implanted. In addition, the second implantable device can be configured to send information about the delivered signals and/or any detected electrical signals, neurochemical signals, and/or ions to the control unit or to a third implantable device. In some cases, the third implantable device can be located within the brain of the mammal at a location that is different from the location of the first implantable device. The third implantable device can be configured to have one or more electrodes and/or one or more microfluidic delivery components configured to deliver neurochemical signals, electrical signals, and/or ions to the mammal's brain. Delivery of these neurochemical signals, electrical signals, and/or ions to the brain can complete a communication loop that originated within a first location of the brain, flowed to a location outside the brain (e.g., a location downstream of a damaged or severed nerve), and flowed back to a second location within the brain.

An implantable device of a system provided herein can include any combination of (a) one or more probes configured to detect neurochemical signals, electrical signals, ions, or combinations thereof, (b) one or more electrodes configured to deliver electrical signals, and (c) one or more microfluidic delivery components configured to deliver neurochemical signals, ions, and/or growth factors. Examples of probes configured to detect neurochemical signals, electrical signals, ions, or combinations thereof include those probes described in U.S. Patent Application Publication No. 2012/0165634. Examples of electrodes configured to deliver electrical signals include those electrodes described in U.S. Patent Application Publication No. 2012/0165634. In some cases, electrical signals can be provided using an electrode such as a neurostimulator (e.g., a Medtronic™ Soletra or Kinetra neurostimulator). Examples of microfluidic delivery components that can be configured to deliver neurochemical signals, growth factors, and/or ions include, without limitation, microfluidic tubes, channels, valves, pathways, input ports, storage regions, and output ports.

In some cases, multiplexed arrays of sensing probes and/or stimulation electrodes can be used. In some cases, a 10×10 electrode array, offering about 100 points in a plane, can be used, thereby covering a substantial volume area. The array can be sized such that a substantial volume can be stimulated by choice, and the activity can be detected in the volume. Time mapping of activity or effect can be carried out using an array. By multiplexing the detection or delivery stimulation, the overhead of data bandwidth and the amount of support electronics can be decreased.

In some cases, an implantable device provided herein can include a single electrode probe for fast scan cyclic voltammetry (FSCV). The single electrode probe can include independent areas (e.g., two independent areas) of active electrode such as pyrolytic carbon or carbon fiber, that, by varying the FSCV impressed voltage, signals representing different neurochemicals can be determined. If the areas are too close together, which would cause interference, the signals can be multiplexed such that the signal is detected quasi simultaneously by measuring one chemical directly after the first chemical was detected. In some cases, an implantable device provided herein can be used to determine the effect of stimulation. Stimulation of two different areas can produce release of different neurochemicals (such as histamine, adenosine, glutamate, and dopamine), and the ratio or absolute amount changes can provide a physiologic effect of interest.

In some cases, one or more chemicals (e.g., dopamine, adenosine, serotonin, and norepinephrine) can be detected using various scan waveforms in FSCV applied to one or more probes.

Figure 1:
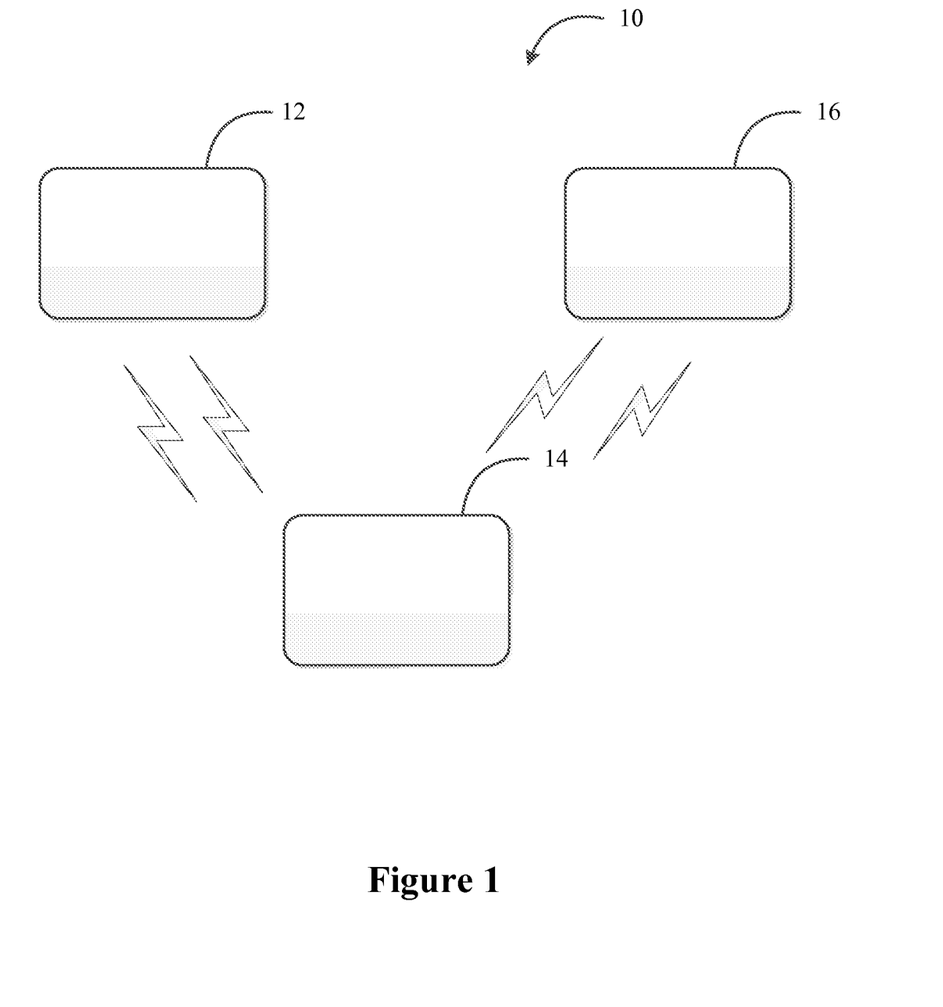
FIG. 1 depicts a system that includes implantable devices for detecting and delivering signals, in accordance with some embodiments.

Referring now to FIG. 1, in some embodiments, a system 10 can include an implantable device 12 containing one or more probes configured to detect neurochemical signals, electrical signals, ions, or combinations thereof. Implantable device 12 can include a control unit and can be in wireless communication with an implantable device 14 containing one or more electrodes configured to deliver electrical signals and/or one or more microfluidic delivery components configured to deliver neurochemical signals, growth factors, and/or ions. In some cases, implantable device 14 can include one or more probes configured to detect neurochemical signals, electrical signals, ions, or combinations thereof. Implantable device 14 can include a control unit and can be in wireless communication with an implantable device 16 containing one or more electrodes configured to deliver electrical signals and/or one or more microfluidic delivery components configured to deliver neurochemical signals, and/or ions. In some cases, implantable device 12 can be positioned within a first location within a mammal's brain, implantable device 14 can be positioned within the mammal's body downstream of a damaged or severed nerve (e.g., proximal to the downstream point of the nerve injury), and implantable device 16 can be positioned within a second location within the mammal's brain.

Figure 2:
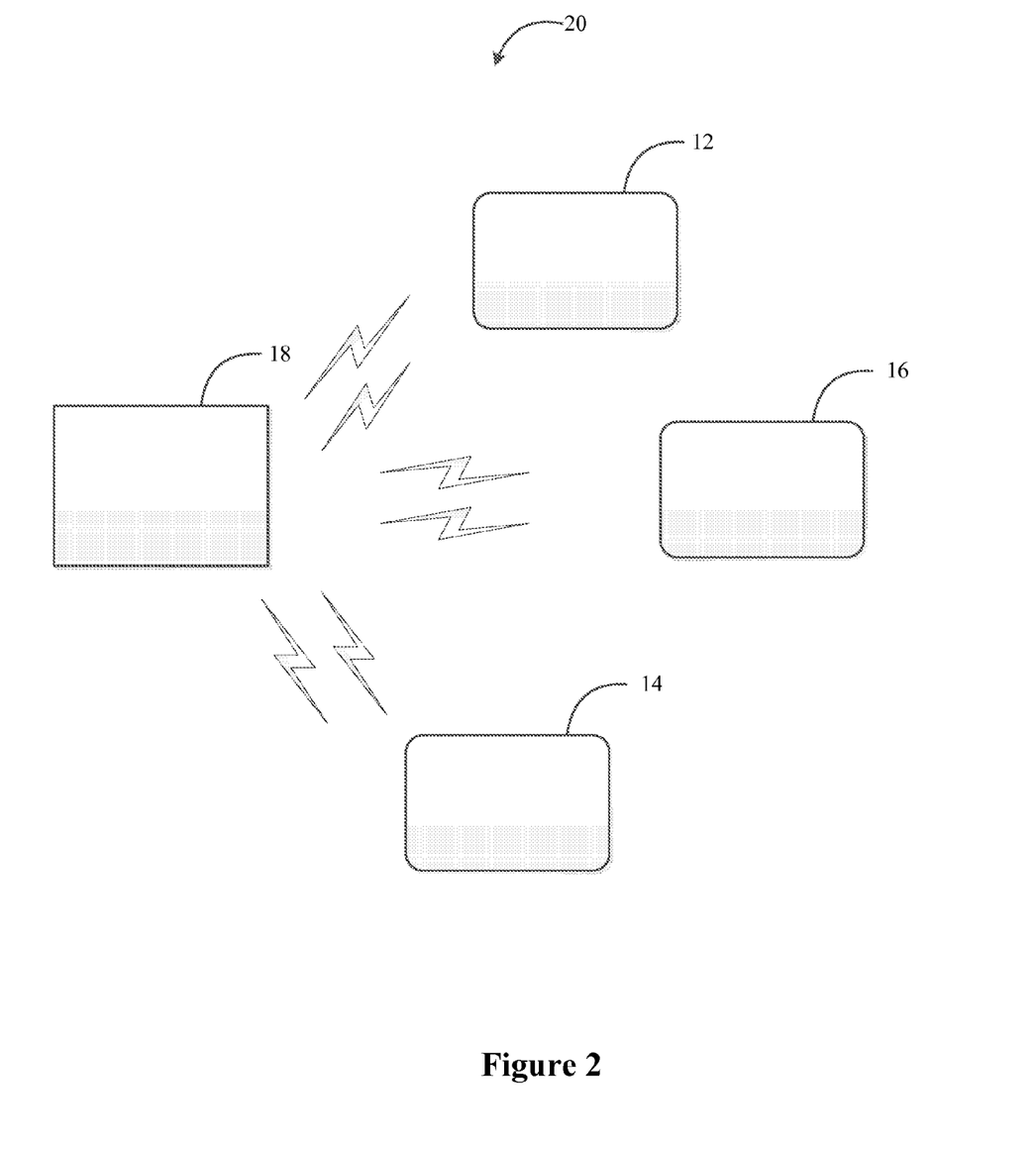
FIG. 2 depicts a system that includes implantable devices for detecting and delivering signals, in accordance with some embodiments.

Referring now to FIG. 2, in some embodiments, a system 20 can include an implantable device 12 containing one or more probes configured to detect neurochemical signals, electrical signals, ions, or combinations thereof, an implantable device 14 containing one or more electrodes configured to deliver electrical signals and/or one or more microfluidic delivery components configured to deliver neurochemical signals, growth factors, and/or ions, and an implantable device 16 containing one or more electrodes configured to deliver electrical signals and/or one or more microfluidic delivery components configured to deliver neurochemical signals, and/or ions. In some cases, implantable device 14 can include one or more probes configured to detect neurochemical signals, electrical signals, ions, or combinations thereof. Each of implantable device 12, implantable device 14, and implantable device 16 can include a control unit and can be in wireless communication with a processing unit 18. Processing unit 18 can be configured to send information to and receive information from each of implantable device 12, implantable device 14, and implantable device 16.

Processing unit 18 can be implanted within the mammal containing implantable device 12, implantable device 14, and implantable device 16 or can be located outside of the mammal containing implantable device 12, implantable device 14, and implantable device 16. In some cases, processing unit 18 can be a hand held communicating device, a personal computing workstation, a server, or the like, and can wirelessly communicate with a display configured to display information indicative of data received by processing unit 18.

In some cases, implantable device 12 can include one or more probes in communication with one or more control units that, for example, can receive information from the individual probes, prepare the data for transmission, and telemeter the prepared data to processing unit 18. In some cases, the control units can receive data from processing unit 18. For example, processing unit 18 can instruct one or more of the control units of implantable device 12 to transmit data from one or more of the probes of implantable device 12 to processing unit 18. In another example, processing unit 18 can instruct individual control units of implantable device 14 to activate one or more electrodes of implantable device 14 to stimulate surrounding tissue and/or to activate one or more microfluidic delivery components to deliver neurochemical signals, and/or ions to surrounding tissue.

Figure 3A:
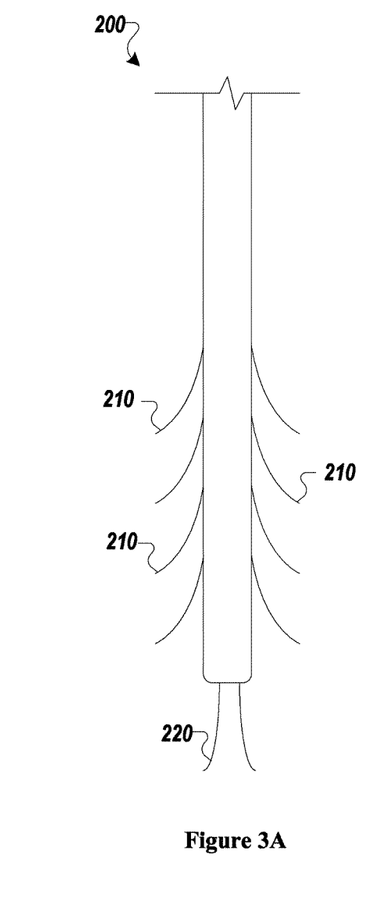
FIGS. 3A-D depict probe assemblies including chemical probes, in accordance with some embodiments.
Figure 3B:
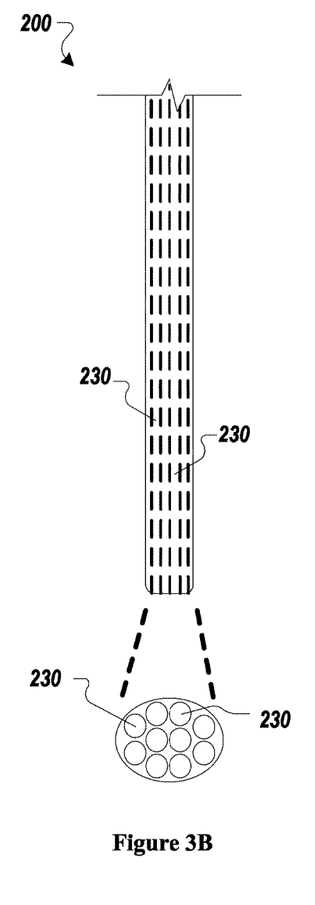
Figure 3C:
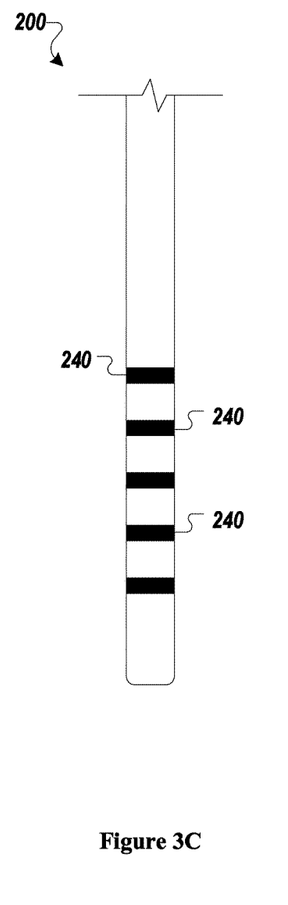
Figure 3D:
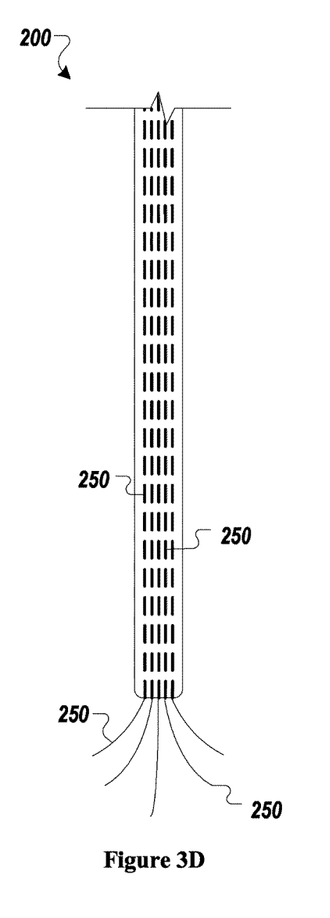

Referring now to FIGS. 3A-D, in some embodiments, an implantable device provided herein can include one or more probe assemblies 200 where each probe assembly 200 can include one or more probes configured to measure a single chemical. In this configuration, a single probe assembly 200 can advantageously measure the level of more than a single chemical. Exemplary measurements performed by chemical probes can include pH level, the concentration of neurochemicals (e.g., dopamine, serotonin, adenosine, norepinephrine, GABA, histamine, acetylcholine, glutamate, and the like), enzymatic activity, electrophysiological activity, and the like. An individual probe assembly 200 can include one or more retractable and advanceable probes such as side chemical probes 210 and distal chemical probes 220 (FIG. 3A). In some embodiments, probe assembly 200 can include one or more chemical probes 230 bundled within an interior lumen of probe assembly 200 (FIG. 3B). Probe assembly 200 can include one or more chemical ring probes 240 around the circumference of probe assembly 200 (FIG. 3C). In some embodiments, probe assembly 200 can include a central lumen through which one or more chemical probes 250 pass and further extend beyond the distal tip of probe assembly 200 (FIG. 3D).

Figure 4A:
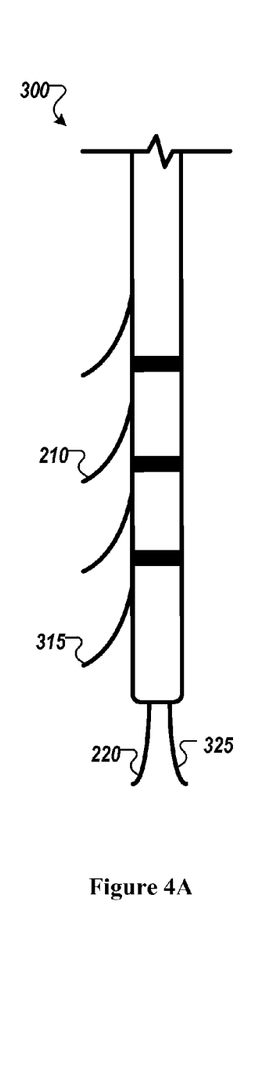
FIGS. 4A-D depict probe assemblies including chemical probes and electrical probes, in accordance with some embodiments.
Figure 4B:
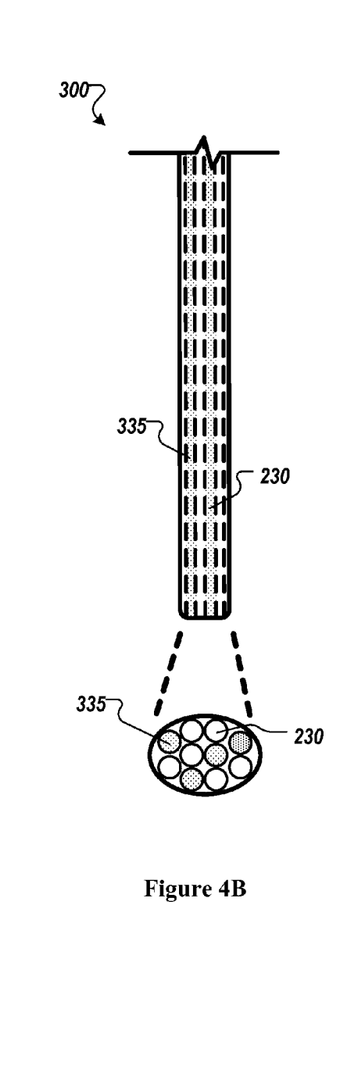
Figure 4C:
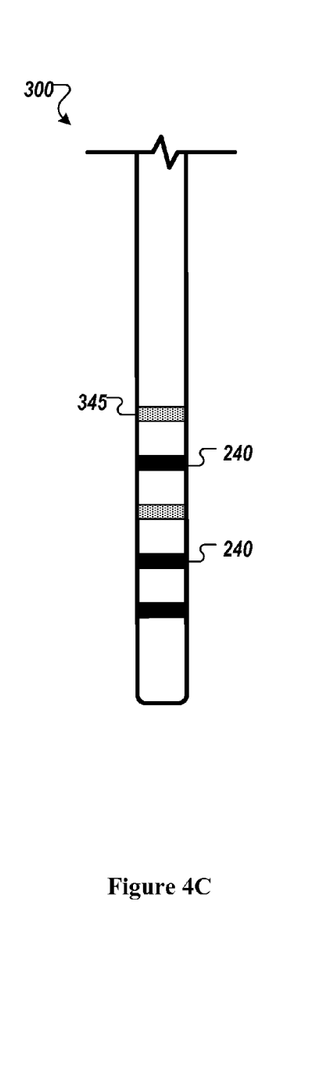
Figure 4D:
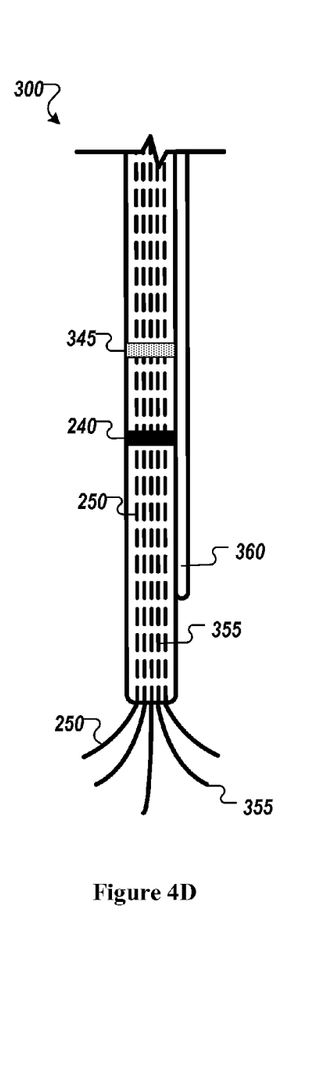

Referring now to FIGS. 4A-D, in some embodiments, an implantable device provided herein can include one or more probe assemblies 300 where each probe assembly 300 can include one or more chemical probes (e.g., chemical probes of the type described in connection with FIGS. 3A-D, and the like) and one or more electrical probes configured to measure a single electrophysiological signal. Exemplary measurements performed by electrical probes can include EEG, EMG, EOG, and the like. An individual probe assembly 300 can include one or more retractable and advanceable probes such as the side chemical probe 210, one or more side electrical probes 315, the one or more distal chemical probes 220, and one or more distal electrical probes 325 (FIG. 4A). In some embodiments, probe assembly 300 can include one or more chemical probes 230 and one or more electrical probes 335 bundled within an interior lumen of probe assembly 300 (FIG. 4B). Probe assembly 300 can include one or more of chemical ring probes 240 and one or more electrical ring probes 345 around the circumference of probe assembly 300 (FIG. 4C). In some embodiments, probe assembly 300 can include a central lumen through which one or more chemical probes 250 and one or more electrical probes 355 pass and further extend beyond the distal tip of probe assembly 300 (FIG. 4D). Probe assembly 300 can include one or more probes (e.g., chemical probes 360, electrical probes (not shown), and the like) mounted on the outside wall of and external to probe assembly 300 (FIG. 4D).

Figure 5A:
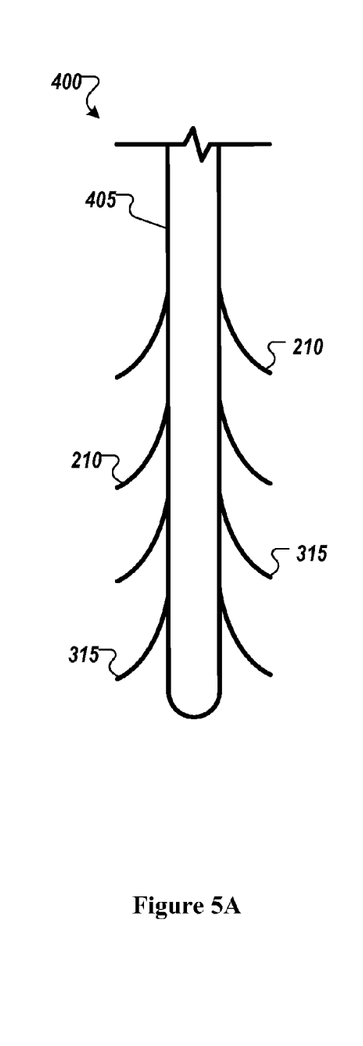
FIGS. 5A-F depict probe assemblies including chemical probes, electrical probes, and electrodes, in accordance with some embodiments.
Figure 5B:
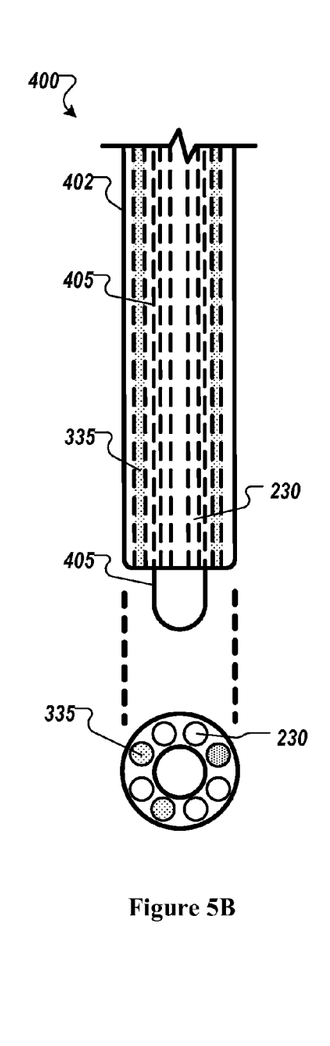
Figure 5C:
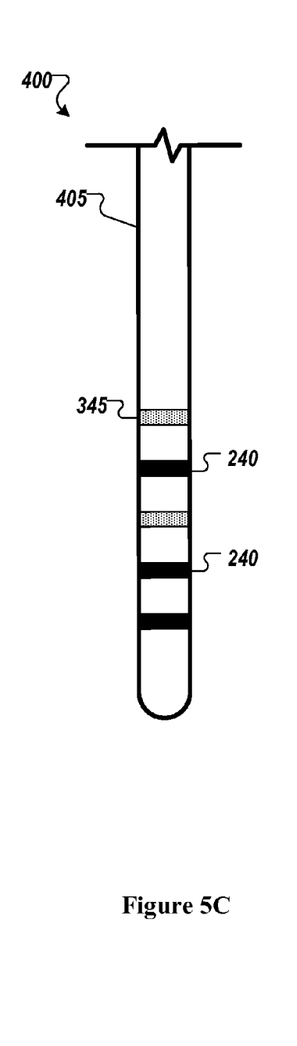
Figure 5D:
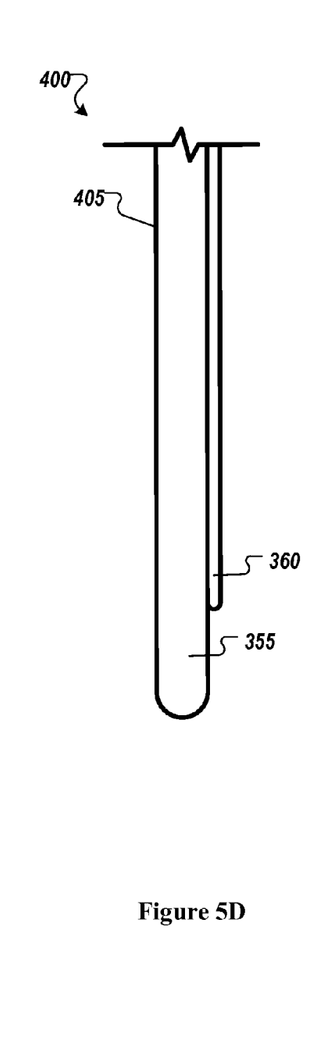

Referring now to FIGS. 5A-F, in some embodiments, an implantable device provided herein can include one or more probe assemblies 400 where each probe assembly 400 can include one or more probes (e.g., probes of the types described in connection with FIGS. 3A-D, FIGS. 4A-D, and the like) and one or more electrodes 405 that can provide an electrical signal to surrounding tissues. Exemplary electrodes 405 can be used to provide electrical signals to nerve or muscle tissue within a mammal downstream of a damaged or severed nerve. An individual probe assembly 400 can include a side chemical probe 210 and a side electrical probe 315 that extend from a sidewall of electrode 405 (FIG. 5A). In some embodiments, probe assembly 400 can include one or more chemical probes 330 and electrical probes 335 bundled around the exterior of electrode 405 and contained, at least partially, within an outer housing 402 (FIG. 5B). Probe assembly 400 can include one or more chemical ring probes 240 and one or more electrical ring probes 345 around the circumference of electrode 405 (FIG. 5C). In some embodiments, probe assembly 400 can include one or more probes (e.g., a chemical probe 360, an electrical probe (not shown), and the like) mounted on the outside wall of and external to electrode 405 (FIG. 5D).

Figure 5E:
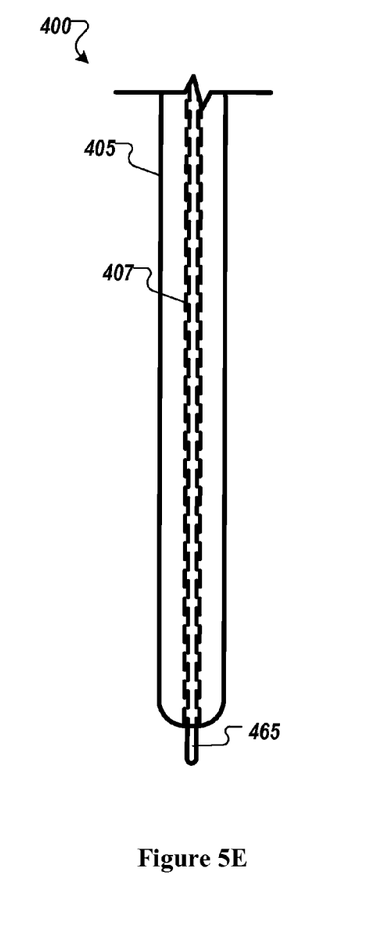
Figure 5F:
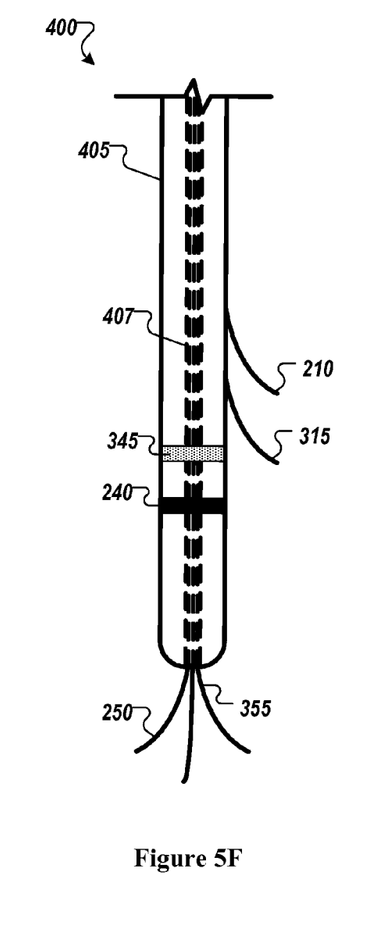

Referring now to FIG. 5E, in some embodiments, a probe assembly 400 can include an electrode 405 with a central lumen 407 through which one or more probes (e.g., electrical probes 465, chemical probes (not shown), and the like) can pass. Referring now to FIG. 5F, in some embodiments, a probe assembly 400 can include an electrode 405 with a central lumen 407 through which one or more of chemical probes 250 and one or more of electrical probes 355 pass and further extend beyond the distal tip of electrode 405. In some cases, a probe assembly can include one or more of ring probes 240 and 345 around the circumference of electrode probe 405 and one or more probes 210 and 215 that extend from the sidewall.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A system comprising:
   a processing unit;
   a first implantable device comprising (i) a first control unit configured to wirelessly communicate with said processing unit and (ii) one or more probes configured to detect, within a first region of a brain of a mammal, neurochemical signals that indicate concentrations of one or more neurotransmitters within said first region of said brain;
   a second implantable device comprising (i) a second control unit configured to wirelessly communicate with said processing unit, (ii) one or more microfluidic delivery components configured to deliver one or more neurochemicals to targeted nerve tissue that is located outside of said brain and downstream of damaged or severed nerve tissue of said mammal and (iii) one or more probes configured to detect neurochemical signals that indicate concentrations of one or more neurotransmitters within a region proximal to said targeted nerve tissue; and
   a third implantable device comprising (i) a third control unit configured to wirelessly communicate with said processing unit and (ii) one or more electrodes or one or more microfluidic delivery components that are respectively configured to deliver electrical signals or neurochemicals to a second region of said brain that is different from said first region of said brain;

wherein said first implantable device is configured to use said first control unit to telemeter first information about said neurochemical signals detected by said first implantable device within said first region of said brain to said processing unit and said processing unit is configured to telemeter a first delivery signal profile derived from said first information to said second implantable device, wherein said second implantable device is configured to receive with said second control unit said first delivery signal profile telemetered from said processing unit and to deliver said one or more neurochemicals to said targeted nerve tissue outside of said brain based on said first delivery signal profile that was derived from said first information about said neurochemical signals detected by said first implantable device within said first region of said brain, wherein said second implantable device is configured to use said second control unit to telemeter second information about said neurochemical signals detected by said second implantable device within said region proximal to said targeted nerve tissue outside of said brain to said processing unit and said processing unit is configured to telemeter a second delivery signal profile derived from said second information to said third implantable device, and wherein said third implantable device is configured to receive with said third control unit said second delivery signal profile telemetered from said processing unit and to deliver electrical signals or neurochemicals to said second region of said brain based on said second delivery signal profile that was derived from said second information about said neurochemical signals detected by said second implantable device within said region proximal to said targeted nerve tissue outside of said brain.

2. The system of claim 1, wherein said second implantable device is configured to be located within a limb, a diaphragm, a genital region, a bladder, a vascular system, or facial tissue of said mammal.

3. The system of claim 1, wherein communication of biological signals between said first region of said brain of said mammal and said targeted nerve tissue is impaired as a result of said damaged or severed nerve tissue, wherein said system is arranged to at least partially restore communication between said first region of said brain of said mammal and said targeted nerve tissue.

4. The system of claim 1, wherein said first implantable device comprises a sensor that is configured to detect different ones of multiple neurochemicals within said first region of said brain by applying electrical signals with different voltage ramps within said first region of said brain.

5. The system of claim 1, wherein:
said first information about said neurochemical signals detected by said first implantable device that is telemetered to said processing unit comprises a brain signal profile that represents particular desired or needed muscular movements of the mammal;
said processing unit is further configured to identify, based on said brain signal profile, the first delivery signal profile, the first delivery signal profile indicating a manner for activating the particular desired or needed muscular movements of the mammal; and said second implantable device is configured to deliver said one or more neurochemicals to said targeted nerve tissue outside of said brain according to said first delivery signal profile.

6. The system of claim 1, wherein:
said third implantable device comprises said one or more microfluidic components that are configured to deliver neurochemicals to said second region of said brain based on said second delivery signal profile.

7. The system of claim 6, wherein said one or more microfluidic delivery components of said second implantable device are configured to deliver to said targeted nerve tissue one or more of adenosine, serotonin, and norepinephrine.

8. The system of claim 1, wherein said processing unit is configured to be implanted within said mammal.

9. The system of claim 1, wherein said second implantable device is further configured to deliver a growth factor to said targeted nerve tissue outside of said brain based on said first information about said neurochemical signals detected by said first implantable device within said first region of said brain.

10. The system of claim 9, wherein said growth factor is selected from the group consisting of nerve growth factor, glia derived neurotrophic factor, and epidermal growth factor.

11. A method comprising:
detecting, using one or more probes of a first implantable device located within a first region of a brain of a mammal, first neurochemical signals that indicate concentrations of one or more neurotransmitters within said first region of said brain;
telemetering, from a first control unit of said first implantable device and to a second control unit of a second implantable device that is located proximal to a targeted nerve tissue downstream of a damaged or severed nerve tissue of said mammal outside of said brain of said mammal, first information about said first neurochemical signals;
receiving, by said second control unit of said second implantable device, said first information about said first neurochemical signals;
delivering, using one or more microfluidic delivery components of said second implantable device, one or more neurochemicals to said targeted nerve tissue based on said first information about said first neurochemical signals;
detecting, using one or more probes of said second implantable device, second neurochemical signals that indicate concentrations of one or more neurotransmitters within a region proximal to said targeted nerve tissue;
telemetering, from said second control unit of said second implantable device and to a third control unit of a third implantable device that is located within a second region of said brain of said mammal, second information about said second neurochemical signals, wherein said second region is different from said first region of said brain of said mammal;
receiving, by said third control unit of said third implantable device, said second information about said second neurochemical signals; and
delivering, using one or more electrodes or one or more microfluidic delivery components of said third implantable device, electrical stimulation or one or more neurochemicals to said second region of said brain of said mammal based on said second information about said second neurochemical signals.

12. The method of claim 11, wherein said first information about said first neurochemical signals that is telemetered from said first control unit of said first implantable device comprises a first delivery signal profile, and said second information about said second neurochemical signals that is telemetered from said second control unit of said second implantable device comprises a second delivery signal profile.

13. A system comprising:
a first implantable device comprising (i) a first control unit and (ii) one or more probes configured to detect, within a first region of a brain of a mammal, neurochemical signals that indicate concentrations of one or more neurotransmitters within said first region of said brain;
a second implantable device comprising (i) a second control unit, (ii) one or more microfluidic delivery components configured to deliver one or more neurochemicals to targeted nerve tissue that is located outside of said brain and downstream of damaged or severed nerve tissue of said mammal and (iii) one or more probes configured to detect neurochemical signals that indicate concentrations of one or more neurotransmitters within a region proximal to said targeted nerve tissue; and
a third implantable device comprising (i) a third control unit and (ii) one or more electrodes or one or more microfluidic delivery components that are respectively configured to deliver electrical signals or neurochemicals to a second region of said brain that is different from said first region of said brain;
wherein said first implantable device is configured to use said first control unit to telemeter first information about said neurochemical signals detected by said first implantable device within said first region of said brain to said second implantable device,
wherein said second implantable device is configured to receive with said second control unit said first information telemetered from said first implantable device and to deliver said one or more neurochemicals to said targeted nerve tissue outside of said brain based on said first information about said neurochemical signals detected by said first implantable device within said first region of said brain,
wherein said second implantable device is configured to use said second control unit to telemeter second information about said neurochemical signals detected by said second implantable device within said region proximal to said targeted nerve tissue outside of said brain to said third implantable device, and
wherein said third implantable device is configured to receive with said third control unit said second information telemetered from said second implantable device and to deliver electrical signals or neurochemicals to said second region of said brain based on said second information about said neurochemical signals detected by said second implantable device within said region proximal to said targeted nerve tissue outside of said brain.

14. The system of claim 13, wherein said first information about said neurochemical signals telemetered from said first control unit of said first implantable device comprises a first delivery signal profile, and said second information about said second neurochemical signals that telemetered from said second control unit of said second implantable device comprises a second delivery signal profile.

* * * * *